(12) United States Patent
Shiuey

(10) Patent No.: US 11,612,477 B2
(45) Date of Patent: Mar. 28, 2023

(54) CORNEAL IMPLANTS

(71) Applicant: Keramed, Inc., Irvine, CA (US)

(72) Inventor: Yichieh Shiuey, San Jose, CA (US)

(73) Assignee: Keramed, Inc., Irvine, CA (US)

(*) Notice: Subject to any disclaimer, the term of this patent is extended or adjusted under 35 U.S.C. 154(b) by 507 days.

(21) Appl. No.: 16/788,582

(22) Filed: Feb. 12, 2020

(65) Prior Publication Data

US 2020/0179100 A1 Jun. 11, 2020

Related U.S. Application Data

(63) Continuation of application No. 14/692,960, filed on Apr. 22, 2015, now Pat. No. 10,675,145, which is a continuation-in-part of application No. 13/979,122, filed as application No. PCT/US2011/053510 on Sep. 27, 2011, now abandoned.

(60) Provisional application No. 61/388,386, filed on Sep. 30, 2010.

(51) Int. Cl.
 *A61F 2/14* (2006.01)
 *A61F 2/00* (2006.01)

(52) U.S. Cl.
 CPC ............ *A61F 2/1451* (2015.04); *A61F 2/142* (2013.01); *A61F 2/1453* (2015.04); *A61F 2/15* (2015.04); *A61F 2002/0081* (2013.01); *A61F 2002/0086* (2013.01); *A61F 2002/0091* (2015.04); *A61F 2210/0014* (2013.01); *A61F 2210/0076* (2013.01); *A61F 2220/0033* (2013.01); *A61F 2230/0006* (2013.01); *A61F 2230/0093* (2013.01); *A61F 2250/0018* (2013.01); *A61F 2250/0026* (2013.01); *A61F 2250/0036* (2013.01); *A61F 2250/0053* (2013.01)

(58) Field of Classification Search
 CPC ........ A61F 2/1451; A61F 2/1453; A61F 2/15; A61F 2/142; A61F 2002/0091; A61F 2002/0081; A61F 2002/0086; A61F 2210/0014; A61F 2210/0076; A61F 2220/0033; A61F 2230/0006; A61F 2230/0093; A61F 2250/0018; A61F 2250/0026; A61F 2250/0036; A61F 2250/0053
 See application file for complete search history.

(56) References Cited

U.S. PATENT DOCUMENTS

| | | | | |
|---|---|---|---|---|
| 4,772,283 | A * | 9/1988 | White | A61F 2/142 623/5.14 |
| 4,842,599 | A * | 6/1989 | Bronstein | A61F 2/142 623/5.15 |
| 6,814,755 | B2 * | 11/2004 | LaCombe | A61F 2/142 623/5.14 |
| 2007/0066706 | A1 * | 3/2007 | Manesis | G02B 1/043 523/106 |
| 2008/0255663 | A1 * | 10/2008 | Akpek | A61F 2/142 623/5.14 |
| 2010/0069915 | A1 * | 3/2010 | Shiuey | A61F 2/147 606/107 |

FOREIGN PATENT DOCUMENTS

WO WO-9820813 A1 * 5/1998 ............. A61F 2/142

* cited by examiner

*Primary Examiner* — Javier G Blanco
(74) *Attorney, Agent, or Firm* — Gearhart Law LLC

(57) ABSTRACT

Reversibly deformable corneal implants for replacing excised corneal tissue, the implants including an optical portion and an anchoring portion having different mechanical properties from each other.

18 Claims, 11 Drawing Sheets

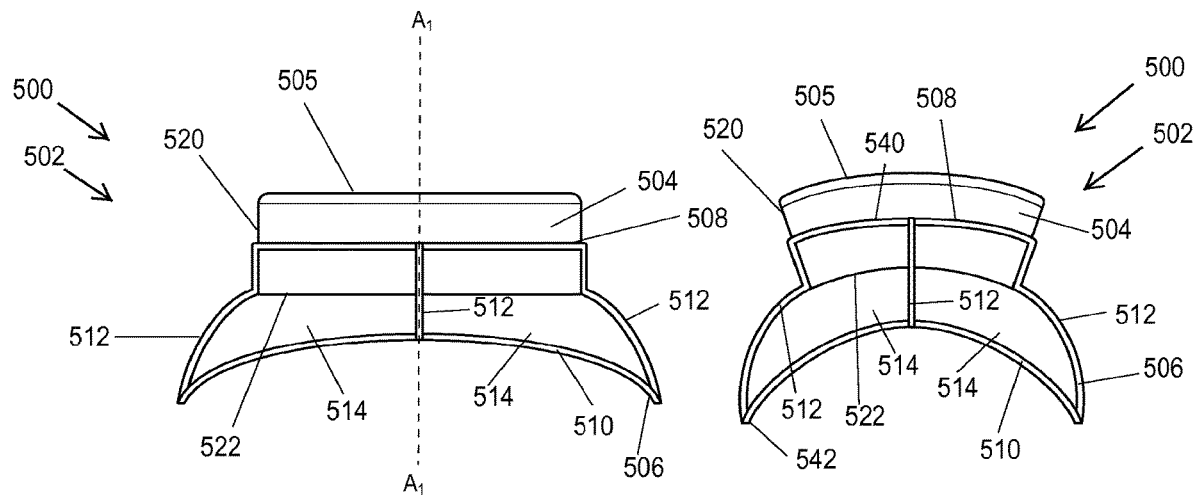
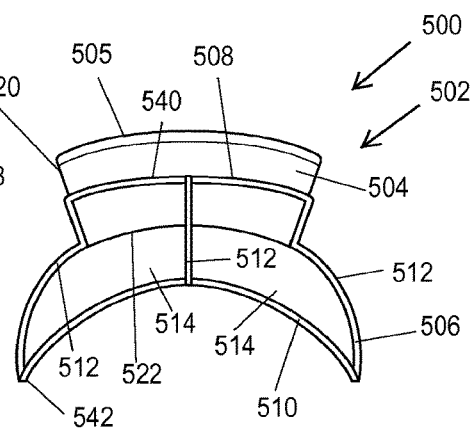
FIG. 14
FIG. 15
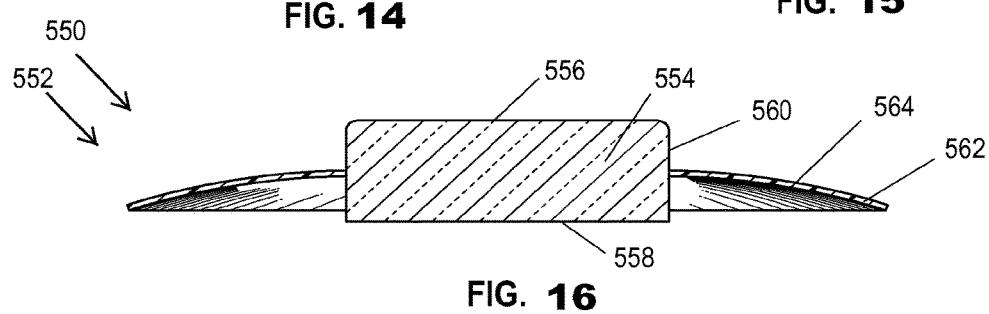
FIG. 16
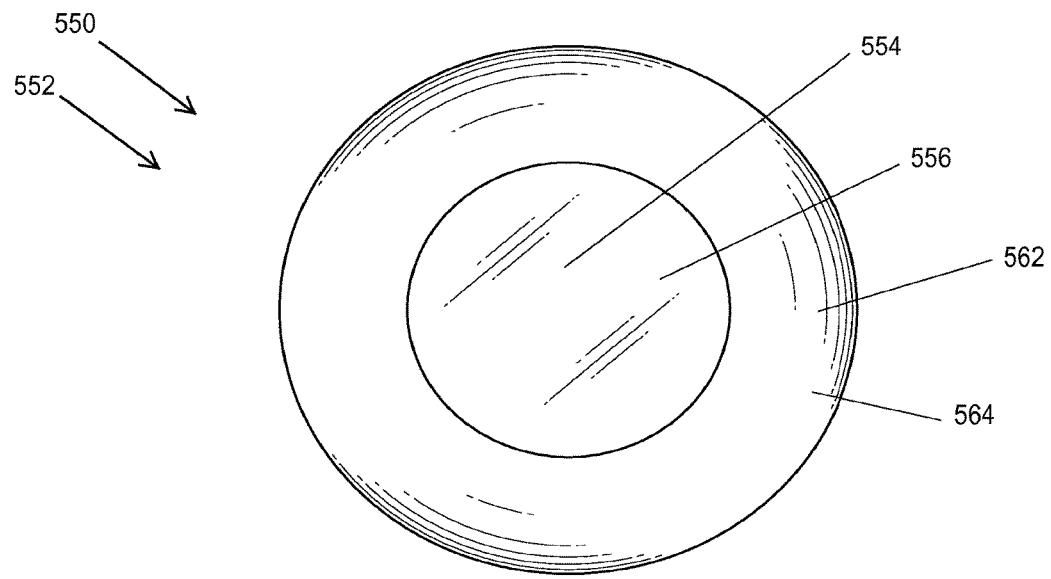
FIG. 17

CORNEAL IMPLANTS

CROSS-REFERENCE TO RELATED APPLICATIONS

This application is a continuation of U.S. Nonprovisional patent application Ser. No. 14/692,960 filed Apr. 22, 2015, titled CORNEAL IMPLANTS, which is a continuation-in-part of U.S. patent application Ser. No. 13/979,122 filed May 21, 2015, titled REVERSIBLY DEFORMABLE ARTIFICIAL CORNEA AND METHODS FOR IMPLANTATION, which is a § 371 National Stage of International Application No. PCT/US2011/053510, filed Sep. 27, 2011, which claims the benefit under 35 U.S.C. 119 of U.S. Provisional Patent Application No. 61/388,386, filed Sep. 30, 2010, the disclosure of which applications are hereby incorporated by reference in their entirety.

BACKGROUND

Corneal implants have a number of different applications. For example, corneal implants play various roles in refractive surgery. These roles include applications where the optical properties of the cornea are modified to achieve a desired effect, e.g. the correction of spherical error, astigmatic error, higher order aberrations or presbyopia. Corneal implants may also be used as prostheses or artificial corneas for replacement of corneal tissue. Throughout this application, the term "artificial cornea" shall mean a corneal implant that replaces at least some excised corneal tissue.

The preciousness of patients' vision and delicateness and intricateness of the human corneal structure and function mean that improvements in corneal implant technologies and implantation techniques are constantly sought after. For example, the inventor previously disclosed the advantages of reversibly deformable corneal implants which can be implanted through an incision size that is less than the maximum width of the implant. In addition, the inventor has previously disclosed reversibly deformable corneal implant prostheses that replace diseased corneal tissue and restore optical function. In some previously disclosed embodiments, these implants are reversibly deformable during implantation and sufficiently flexible to avoid damaging corneal tissue during the physiologic deformation of the cornea which occurs with blinking. Corneal implants and methods for their implantation into corneal pockets are also described in commonly owned U.S. Pat. Nos. 7,223,275 and 8,029,515; U.S. Patent Publication Nos. 2004/0243160; 2006/0173539; US2010/0069915; and PCT Publication No. WO 2008/055118. The disclosures of these applications are hereby incorporated by reference into this application in their entirety.

Most artificial corneas have been implanted in a penetrating fashion where the artificial cornea is in direct contact with the aqueous fluid in the eye. Because the synthetic materials which have been used for artificial corneas have not been able to completely integrate with the surrounding corneal tissue, bacteria from the surface of the eye can travel along microscopic openings between the artificial cornea and the circumscribing corneal tissue resulting in intraocular infection (endophthalmitis) which can cause loss of the eye.

In addition, extrusion of artificial corneas can result from any one or more of three primary causes herein. The first cause is the use of relatively large incisions for implantation. For example, the AlphaCor™ Artificial Cornea from Addition Technology, Inc., requires a 16 mm incision for implantation into an intralamellar pocket. The AlphaCor artificial cornea must be sutured in place with resorbable nylon sutures. The cornea has avascular tissue and heals poorly. Once the nylon sutures dissolve over a period of several years, the corneal scar tissue may not be sufficient in strength to hold the artificial cornea within the cornea, commonly resulting in extrusion.

A second potential cause of extrusion of artificial corneas is interference with corneal physiology. For example, some artificial corneas have been made from materials that are impermeable to both oxygen and glucose e.g. polymethylmethacrylate. Polymethymethacrylate has effectively no measurable oxygen permeability and therefore has a dK of zero Barrer. Over time the lack of adequate oxygenation and nutrition of the corneal tissues can result in melting of the cornea followed by extrusion.

A third potential cause of extrusion of artificial corneas is excessive rigidity of the artificial cornea. Very stiff materials, such as polymethylmethacrylate which has a Young's modulus between 1800 and 3100 MPa, can erode through the cornea over time. Such erosion can result from blinking of the eyelid which deforms the cornea and can abrade corneal tissue as the tissue repeatedly rubs against the rigid implant material. Such erosion can in turn lead to extrusion.

In addition to these problems, present artificial corneas can be uncomfortable for the patient. For example, the patient's tear film can be disrupted by the implant projecting above or falling below the surface of the surrounding cornea. Projection of the implant above the surface of the cornea can also cause abrasion of the inside of the eyelid. An implant with an optic below the surface of the surrounding cornea can also allow deposition of mucus into the "hole," which can obscure the vision.

For these reasons, it would be desirable to provide improved artificial corneas which overcome at least some of the problems noted above. In particular, it would be desirable to provide artificial corneas and methods for their implantation where the risk of infection of the eye is reduced. It would be further desirable to provide artificial corneas which are resistant to extrusion due to any of the reasons cited above. Additionally, it would be desirable to provide artificial corneas which are comfortable for the patient and which maintain the tear film with minimum disruption. In addition, there is a need for artificial corneas made from a plurality of materials having disparate mechanical properties while being reversibly deformable (i.e. implantable through an incision that is smaller than the relaxed implant), and configured to replace excised corneal tissue. At least some of these objectives will be met by the disclosures described below.

SUMMARY

The present disclosure overcomes at least some of the problems noted above with prior artificial corneas. In some embodiments, the artificial corneas are made to be implanted within the lamellae of the cornea without penetration into the anterior chamber of the eye. By avoiding such penetration, the risk of eye infection (endophthalmitis) is greatly reduced. In some embodiments, the artificial corneas or portions thereof are designed to be sufficiently flexible and durable so that they can be implanted through small incisions into a corneal lamellar pocket when the size of the pocket entry incision is smaller than the artificial cornea in its relaxed state. Such implantation is advantageous both because it further inhibits the intrusion of bacteria around the implant into the anterior chamber and because it helps anchor the implant which allows the device to be self-retaining even without sutures or adhesives. Usually, however, the implant will be at least somewhat more rigid than the corneal tissue which will allow the implant to maintain an optically advantageous shape after implantation.

With prior artificial corneas, it has not been possible to consistently fit the artificial cornea to match the natural shape of the cornea. This is important because a mismatch between the artificial cornea optic and the surface of the cornea causes clinically significant problems. In the case of the Boston Artificial Cornea, elevation of the optic above the level of the carrier donor cornea causes a persistent foreign body sensation for the patient and necessitates the continuous use of a bandage contact lens to prevent abrasion of the conjunctiva on the inside of the eyelid. The optic of the Alphacor™ on the other hand sits below the level of the host cornea by 300 microns, which creates a divot or hole that continuously accumulates debris such as mucus and thereby limits the visual improvement of the patient.

In some embodiments, the artificial cornea is implanted into the cornea using incisions with very precise dimensions. The precision of the dimensions will allow the artificial cornea to fit exactly into the cornea so that the surface of the artificial cornea will be flush with the surface of the artificial cornea optic and there will be no gap between the optic and corneal tissue. The ability to create corneal incisions with this high level of precision has only become possible recently with the availability of the femtosecond laser and mechanical corneal pocket makers. In some examples the corneal incisions will be created with a femtosecond laser which commonly has a tolerance of about +/−3 microns. In alternate examples the corneal pocket incision can also be created with a mechanical corneal pocket maker, which generally will have a tolerance of +/−50 microns or better. A manually made pocket can also be used to implant the artificial corneas disclosed herein, however, it would be impossible to assure that the optic would be flush with the surface of the host cornea because the human hand is not capable of making incisions with a precision of +/−50 microns.

In some embodiments, the incisions that create the opening for the optic of the artificial cornea of the present disclosure will also precisely match the angulation of the optic, i.e. the incision of the cornea which abuts the optic would match the angulation of the optic within +/−30 degrees and in some examples +/−10 degrees. For example, if the side of the optic creates a 90 degree angle with the plane created by the junction of the rim and the optic, the abutting corneal incision should also be 90 degrees to the plane created by the junction of the rim and the optic.

In alternate examples, the corneal incisions will be made to excise a volume of corneal tissue having a shape which is similar to the three-dimensional shape of the artificial cornea (FIG. 9A). Such an interference or interlocking fit of the artificial cornea with the corneal tissue can help retain the device within the cornea as shown in FIG. 9B.

In a specific example of the present disclosure, the artificial cornea has a center optic which will be machined to a very close tolerance to maintain a preselected optic height within a tolerance in the range from ±50 μm or less. As 50 nm is the average thickness of the epithelium over the cornea, and the corneal epithelium will be able to respond by thinning or thickening to offset any difference between the surface level of the artificial cornea and that of the native cornea. Thus, by carefully controlling the depth of the corneal pocket to within a similar tolerance or closer, the optic height of the artificial cornea can be matched with that of the native cornea to preserve the tear film over the eye and artificial cornea and increase patient comfort. The optic height will typically be maintained between 200 μm to 400 μm to allow a sufficient thickness of the natural corneal tissue to cover the rim of the artificial cornea so there is a decreased risk of erosion through tissue. In cases of abnormally thick corneas, such as commonly found in patients suffering from corneal edema due to endothelial failure, the optic height may be as much as 800 μm to compensate for such increased thickness.

Thus, in some embodiments, a reversibly deformable artificial cornea comprises a monolithic body having a center optic surrounded by an annular rim. By "monolithic," it is meant that the center optic and the rim are a single, continuous body of material free from seams, joints and the like. For example, the artificial cornea may be formed from a single blank or block of material typically a polymeric hydrogel of a type commonly employed in forming intraocular lenses (IOL's) such as commercially available from Benz Research. The polymeric hydrogel material could also have both hydrophobic and hydrophilic properties, such as a copolymer of hydroxyethyl methacrylate and methylmethacrylate which has undergone plasma surface treatment. Alternatively, the artificial cornea could be molded, machined, or laser cut from a material comprising an interpenetrating network or a collagen-based hydrogel.

The monolithic body, when hydrated, will have a diameter in the range from 4 mm to 10 mm. The center optic will have a diameter in the range from 3 mm to 9 mm and an optic height (D, FIG. 4) in the range from 200 μm to 800 μm. The manufacturing tolerance of the optic height will be +/−50 microns or less, to allow a precise fit to the surrounding recipient corneal tissue. The annular rim will have an annular width in the range of 0.5 mm to 4.5 mm and a median thickness in the range from 50 μm to 200 μm. In some examples the polymeric hydrogel will be selected to have a modulus in the range from 0.3 MPa to 100 MPa when fully hydrated. In some examples the tensile strength is at least 1.5 MPa and the elongation to break is at least 100%. Suitable body materials should be at least partially permeable to oxygen, typically having an oxygen permeability (dK) of at least 3 Barrer. Exemplary materials with excellent oxygen permeability, e.g. dK of at least 60 include: Lotrafilcon A, Lotrafilcon B, Balafilcon A, Comfilcon A, Senofilcon A, Enfilcon A and Galyfilcon A.

In some embodiments, the annular rim of the corneal implant circumscribes a posterior edge of the center optic. Further, an anterior surface of the center optic is usually convexly shaped to provide a refractive power generally equal to or consistent with a native cornea, typically being in the range from 30 diopter to 70 diopter, when implanted in the cornea. Usually, the anterior surface of the center optic will be convexly shaped and the posterior surface will be concavely shaped. The radius of curvature of the posterior optic and the rim will typically be consistent with the range of curvature of the native cornea being in a range from 6.2 mm to 10 mm.

In some embodiments, the annular rim will have a plurality of apertures to allow passage of nutrients and oxygen therethrough. As the rim will be implanted between adjacent lamellar surfaces of the cornea, it is important that nutrients be able to pass therethrough to maintain health of the corneal tissue. In some embodiments, the apertures will occupy from 10% to 90% of the annular area of the rim, typically occupying about 33% of the area. In some embodiments the apertures are round holes disposed uniformly about the annular rim, but they could take a number of other geometries such as crenellations in the outer edge of the annular rim.

In a further example of the present disclosure, methods are disclosed for implanting an artificial cornea in a cornea to replace an impaired center region of the cornea comprise forming a central anterior opening having a posterior surface surrounded by a peripheral sidewall in the cornea. The opening will in some examples have a uniform depth, typically in the range from 200 μm to 800 μm, where the depth will be selected to match the height of the peripheral wall of the center optic of the implant, within ±50 μm in some examples. The artificial cornea is implanted within the central anterior opening so that the peripheral thickness or wall height of the center optic will match the peripheral sidewall of the central anterior opening to within a tolerance of ±50 μm to provide the advantages discussed above.

In specific embodiments of the method, in addition to forming the central anterior opening, a lamellar pocket will be formed over at least a portion of the peripheral sidewall of the central anterior opening and a rim portion of the implant will be inserted into the lamellar pocket in order to anchor the implant in the opening. Typically, the lamellar pocket will fully circumscribe the central anterior opening and the annular rim will fully extend around the implant. In still further exemplary embodiments the lamellar pocket is formed around the periphery of the posterior surface of the central anterior opening and the annular rim which enters the lamellar pocket is disposed around a posterior edge of the center optic of the corneal implant.

In some embodiments, the central anterior opening is formed to have a diameter smaller than that of the center optic, typically from 70% to 99% of the center optic diameter, so that the partially elastic corneal tissue can seal closely around the peripheral wall of the implant to help prevent extrusion of the implant after sutures are removed, to inhibit ingrowth of epithelial cells, inhibit the entry of bacteria, and prevent loss of fluid from the anterior chamber. The artificial cornea may be implanted within the central anterior opening by one of two different techniques. In the first technique, the artificial cornea is constrained (i.e. deformed) to reduce its width and introduced through an upper surface of the anterior central opening in a posterior direction. The artificial cornea can be released from constraint within the central anterior opening so that it assumes its unconstrained geometry to occupy the volume of the central opening, usually with the annular rim inserting into the lamellar pocket. Alternatively, a separate lateral opening can be formed from the side of the eye into the central anterior opening and the constrained artificial cornea introduced therethrough.

In some embodiments, the artificial cornea is adapted to support growth of a viable corneal epithelium over the periphery of the anterior face of the optic. Establishing a viable epithelium over the peripheral anterior surface will advantageously provide a biological seal around the edge of the anterior face of the optic to prevent bacteria from entering the corneal pocket through the junction of the raised optic and the corneal stroma. In some examples the center of the optic will remain free of corneal epithelium after implantation which will allow the central surface of the optic principal (which is critical to the optical performance) to remain optically smooth even when the patient's eye is not able to form a smooth optically good epithelium. In some embodiments, the patient's corneal epithelium will be able to grow onto the periphery of the anterior face of the optic over a width in the range from 0.1 mm to 1 mm.

Promoting the growth of a viable corneal epithelium over the periphery of the anterior optic may be achieved by coating or covalently bonding certain biological molecules which promote such growth, such as extracellular matrix proteins or growth factors, over the periphery of the anterior face of the optic, usually to a width in the range set forth above. Suitable biological molecules include collagen, fibronectin, laminin, fibronectin adhesion-promoting peptide sequence (H-trp-gln-pro-pro-arg-ala-arg-ile-OH) (FAP), and epidermal growth factor. In other examples the periphery of the optic can be made porous or roughened in texture to allow corneal epithelial cells to bind more easily to the surface of the periphery of the anterior optic face.

Many materials which could be used for the manufacture of the artificial cornea will generally not support the growth of corneal epithelial cells without special surface treatment as described above. In such cases, the artificial cornea can be formed of such a non-growth-promoting material with the periphery treated to promote growth. In the case of an artificial cornea formed from a material that does inherently support epithelial growth, such as collagen or a collagen derivative, a polymer that will not support the growth of epithelium e.g. a silicone or a methacrylate, may be coated over the central optic surface to keep the central optic surface free of epithelium.

In some embodiments, different portions of an artificial cornea are made from materials embodying different mechanical properties. For example, in some embodiments an anchoring portion of the artificial cornea is made from a material that has different mechanical properties from that of the optical portion of the artificial cornea. In some of these embodiments, different mechanical properties are achieved by using different materials. In other embodiments, different mechanical properties are achieved by subjecting different portions of an artificial cornea made from a single material to different treatments, such as mechanical, radiation (e.g., electromagnetic), heat, and/or chemical treatments. In still further embodiments, different mechanical properties are achieved through the use of both different materials and different material treatments. Artificial corneas having discrete portions with different mechanical properties can improve patient comfort, improve visual quality, reduce the chances of extrusion and improve the artificial cornea's ability to reversibly deform. In general optical portions which are stiffer will result in better optical performance, but may result in more patient discomfort. In general, the stiffer the anchoring portion, the less likely the artificial cornea will spontaneously extrude from the eye, but there may be more discomfort and greater risk of erosion through the corneal tissue over time.

In addition, artificial corneas having an optical portion with a first set of mechanical properties and an anchoring portion with a second set of mechanical properties in accordance with the present disclosure, can allow for artificial cornea structures that promote nutritive permeability (e.g. by incorporating a large amount of empty space into the anchoring portion) without increasing the risk of extrusion post-implantation.

In some embodiments, the amount of material used for the anchoring portion of the artificial cornea is reduced or minimized. This can reduce the overall weight of the artificial cornea, reduce the chances of its extrusion, improve its reversible deformability characteristics and improve the nutritive permeability of the artificial cornea.

With the above in mind, in one aspect a corneal implant comprises an artificial cornea for replacing excised corneal tissue, the artificial cornea comprising a relaxed state and a deformed state and being reversibly deformable such that the artificial cornea can return to the relaxed state from the deformed stated and can be implanted into an eye through an opening that is less than a width of the artificial cornea in the relaxed state; the artificial cornea further comprising an optical portion and an anchoring portion, the optical portion comprising a material with a first set of mechanical properties, and the anchoring portion comprising a material with a second set of mechanical properties.

In another aspect a corneal implant comprises an artificial cornea for replacing excised corneal tissue, the artificial cornea comprising a relaxed state and a deformed state and being reversibly deformable such that the artificial cornea can return to the relaxed state from the deformed state and can be implanted into an eye through an opening that is less than a width of the artificial cornea in the relaxed state; the artificial cornea further comprising an optical portion and an anchoring portion, the optical portion comprising a material that has been treated differently from the anchoring portion.

In another aspect a corneal implant comprises an artificial cornea for replacing excised corneal tissue, the artificial cornea comprising a relaxed state and a deformed state and being reversibly deformable such that the artificial cornea can return to the relaxed state from the deformed stated and can be implanted into an eye through an opening that is less than a width of the artificial cornea in the relaxed state; the artificial cornea further comprising an optical portion and an anchoring portion, the optical portion comprising a material with a first set of mechanical properties, and the anchoring portion comprising a material with a second set of mechanical properties, the second set of mechanical properties selected to self-retain the anchoring portion within a cornea.

In a further aspect a corneal implant comprises an artificial cornea for replacing excised corneal tissue, the artificial cornea comprising a relaxed state and a deformed state and being reversibly deformable such that the artificial cornea can return to the relaxed state from the deformed state and can be implanted into an eye through an opening that is less than a width of the artificial cornea in the relaxed state; the artificial cornea further comprising an optical portion and an anchoring portion, the anchoring portion comprising a material that has been treated differently from the optical portion in order to self-retain the anchoring portion within a cornea.

In yet a further aspect a corneal implant comprises an artificial cornea for replacing excised corneal tissue, the artificial cornea comprising a relaxed state and a deformed state and being reversibly deformable such that the artificial cornea can return to the relaxed state from the deformed stated and can be implanted into an eye through an opening that is less than a width of the artificial cornea in the relaxed state; the artificial cornea further comprising an optical portion and an anchoring portion; the optical portion comprising a side wall, a groove disposed in the side wall, and a first material; the anchoring portion comprising a second material, an inner ring, and an outer ring such that there is open space between the inner ring and the outer ring and such that the inner ring is coupled to the groove; wherein the first material comprises an elastic modulus that is different from the elastic modulus of the second material; wherein the first material comprises a tensile strength that is different from the tensile strength of the second material; wherein the first material comprises an elongation to break ratio that is different from the elongation to break ratio of the second material; and wherein at least one of the elastic modulus, tensile strength, and elongation to break ratio of the second material is selected to self-retain the anchoring portion within a cornea.

BRIEF DESCRIPTION OF THE DRAWINGS

FIG. 14 is a side view of the corneal implant of FIG. 10 showing the implant in an example deformed state in which the anchoring portion is deformed and the optical portion is relaxed.

FIG. 15 is a side view of the corneal implant of FIG. 10 showing the implant in a deformed state in which both the anchoring portion and the optical portion are deformed.

FIG. 16 is a side cross-sectional view of a further embodiment of a corneal implant in accordance with the present disclosure.

FIG. 17 is a front view of the corneal implant of FIG. 16.

DETAILED DESCRIPTION

Figure 1:
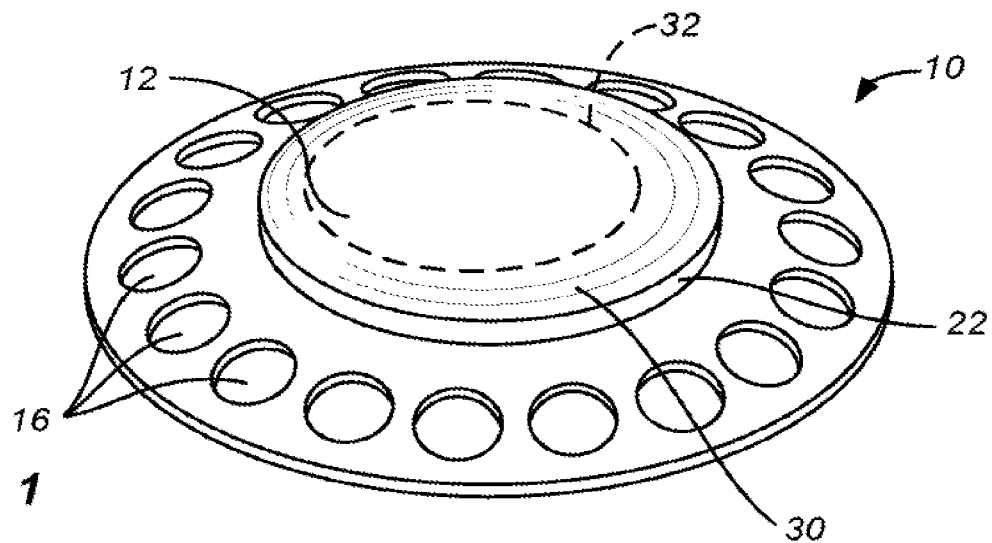
FIG. 1 is a perspective view of an artificial cornea constructed in accordance with the principles of the present disclosure.

Various embodiments are described herein in detail with reference to the drawings, wherein like reference numerals represent like parts and assemblies throughout the several views. Reference to various embodiments does not limit the scope of the appended claims. Additionally, any examples set forth in this specification are not intended to be limiting and merely set forth some of the many possible embodiments for the appended claims.

Figure 2:
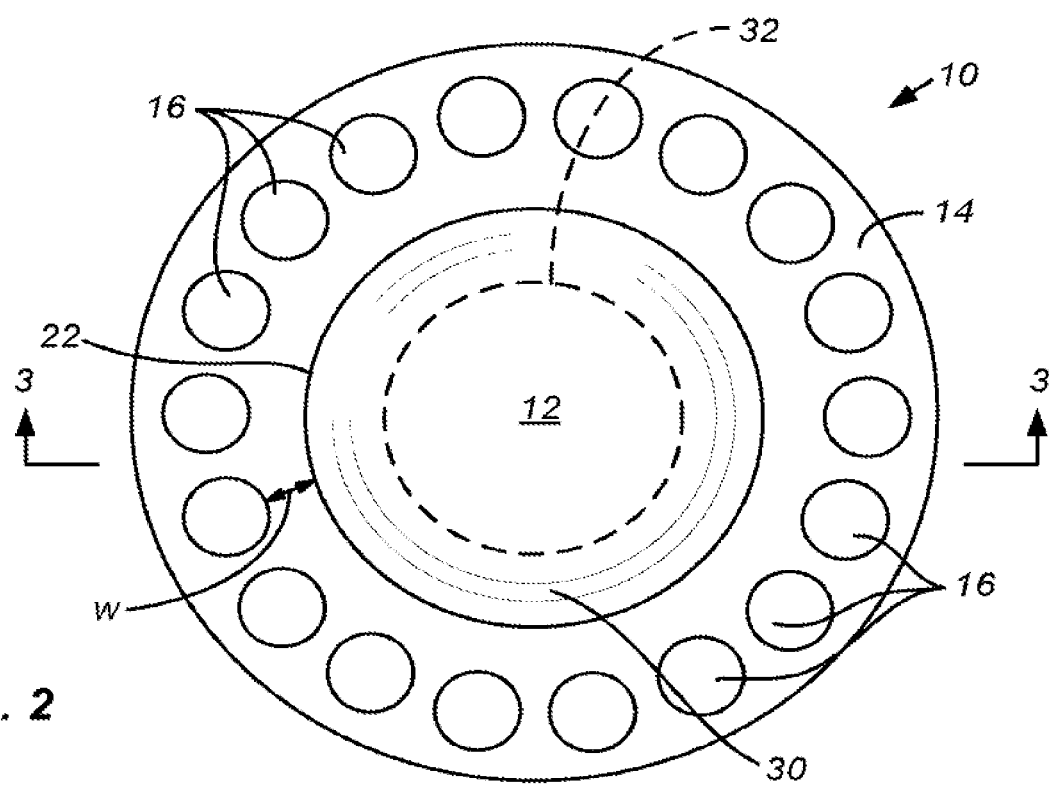
FIG. 2 is a front view of the artificial cornea of FIG. 1.
Figure 3:
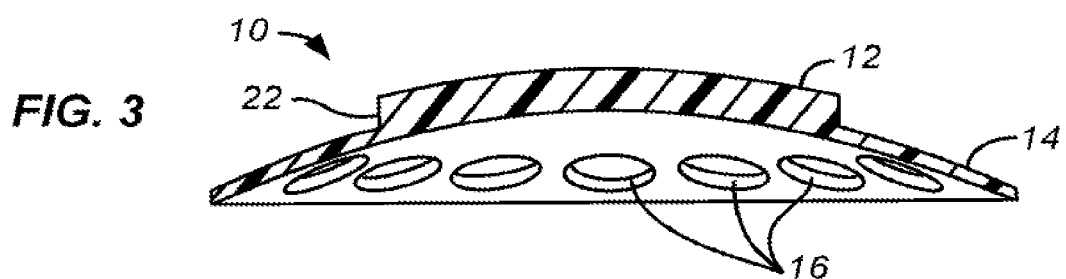
FIG. 3 is a cross-sectional view of the artificial cornea of FIGS. 1 and 2 taken along line 3-3 of FIG. 2.

Referring to FIGS. 1-3, an artificial cornea 10 in accordance with the principles of the present disclosure comprises a center optic 12 surrounded by an annular rim 14. A plurality of apertures 16, typically circular holes, are formed fully through the annular rim to allow the passage of nutrients therethrough after implantation. As illustrated, the apertures 16 comprise about 33% of the total area of the annular rim 14, but the total open or void area provided by the apertures could be anywhere in the range from 10% to 90% of the total area.

In some examples the artificial cornea 10 is formed to be a monolithic structure, i.e., a structure having no seams or joints and in some examples formed from a single blank or block of material. For example, the artificial cornea 10 may be machined from a block of suitable hydrogel polymer.

Optionally, a peripheral edge of the anterior surface of the center optic may be modified (or left unmodified) to support the growth of an epithelium over an annular region with a width typically in the range from 0.1 mm to 1 mm. As described above, when the center optic material inherently inhibits the growth of the epithelium, the annular region (bounded by broken line 32) may be modified by coating or depositing an epithelial-growth promoting material. Roughening the texture of the annular region or making the annular region porous can also promote the growth of epithelium over the annular region. In addition, the anterior region of the center optic inside of broken line 32 may be coated or deposited with a material which inhibits epithelial growth, such as a silicone or methacrylate.

Figure 4:
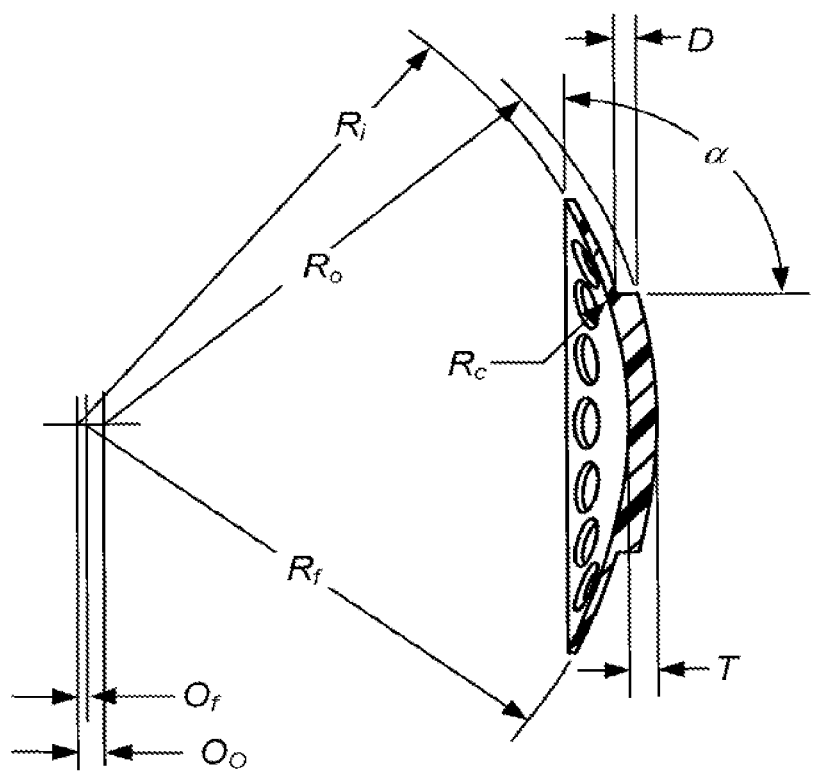
FIGS. 4 and 5 illustrate the locations of the dimensions set forth in Table 1 hereinafter.
Figure 5:
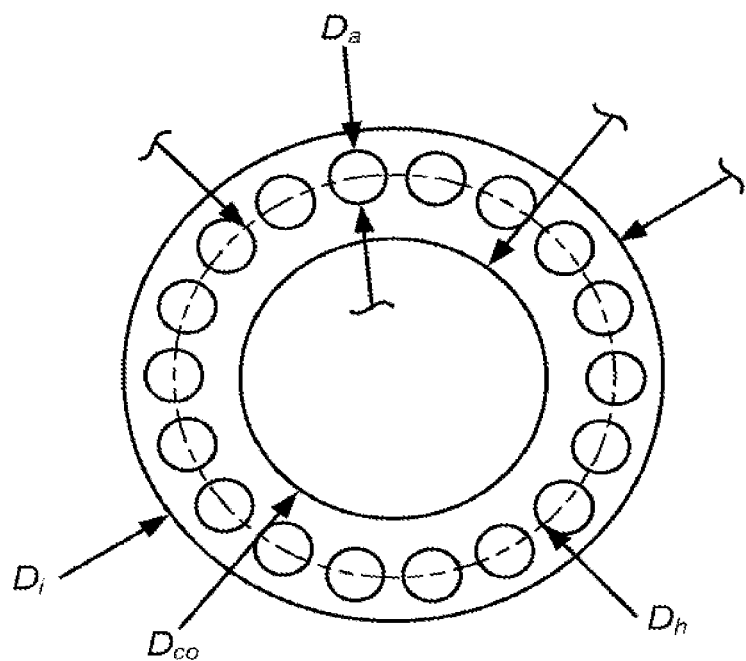

Typical ranges and values for the dimensions of an artificial cornea 10 are set forth in Table 1 below, referring to FIGS. 4-5. These dimensions are given for the artificial cornea in its fully hydrated state:

| Dimension | Specific Value | Tolerance |
|---|---|---|
| D | 0.200 mm | ±0.050 mm |
| Ri | 7.6 mm | ±0.127 mm |
| Ro | 7.7 mm | 0.127 mm |
| Rc | 0.1 mm | Reference |
| Rf | 7.6 mm | ±0.127 mm |
| Of | 0.05 mm | ±0.050 mm |
| Oo | 0.256 mm | ±0.050 mm |
| A | 90° | ±100 |
| Da | 0.8 mm | ±0.127 mm |
| Df | 8 mm | ±0.254 mm |
| Dco | 4 mm | ±0.127 mm |
| Dh | 5.25 mm | Reference |

While the annular rim 14 in some examples includes apertures 16 such as circular holes, it may be further desirable that at least an innermost region of the annular rim adjacent to an outer peripheral wall 22 and the center optic 12 (FIGS. 1-3) remain solid. This solid section of the rim immediately adjacent to the optic will help prevent bacterial ingress and intrusion of epithelial cells in cases where the posterior cornea behind the optic has been excised, which may be necessary when the posterior cornea is very opaque. In some examples a width W (FIG. 3) of solid material in the range from 0.25 mm to 0.75 mm will be maintained. The apertures or other open regions of the rim will thus be disposed radially outwardly from this solid region.

Figure 8A:
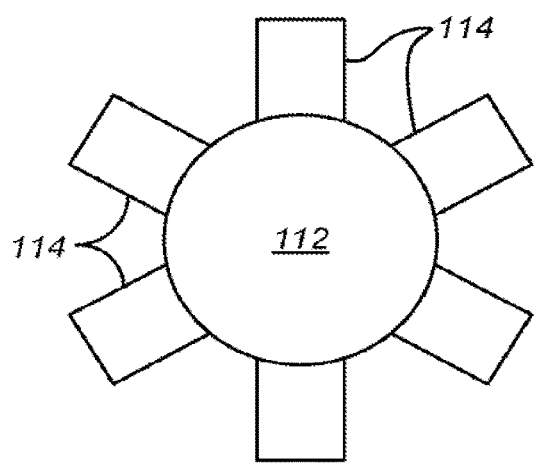
FIGS. 8A through 8D illustrate exemplary rim designs for the artificial cornea of the present disclosure.
Figure 8B:
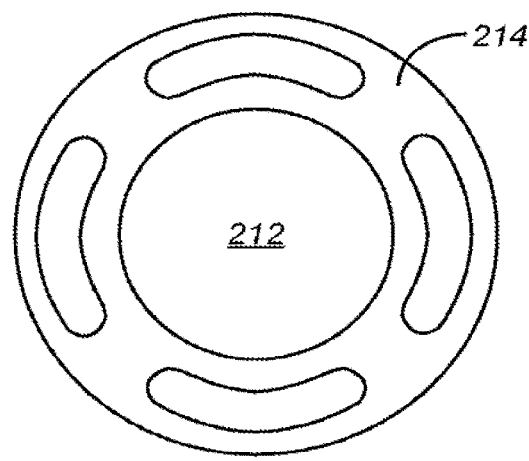
Figure 8C:
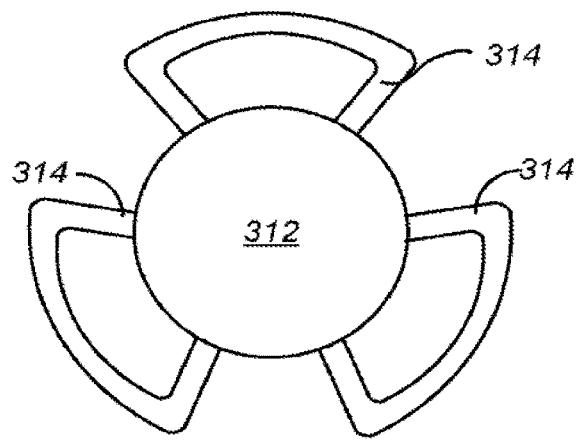
Figure 8D:
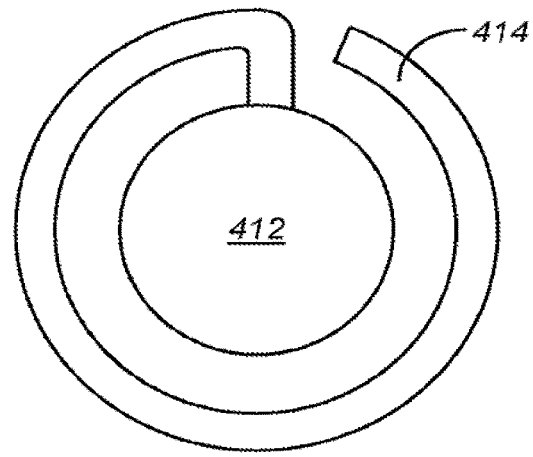

In other embodiments, a rim 114 which surrounds center optic 112 may be discontinuous or may consist of material with hollow sections or a scaffold structure as shown in FIG. 8A. Other variations include a discontinuous rim 214 surrounding a center optic 212 (FIG. 8B), an annular rim 314 with oblong cutouts surrounding a center optic 312 (FIG. 8C), and a scaffold rim 414 surrounding a center optic 412 (FIG. 8D). In some examples of these embodiments, the rim 114, 214, 314 or 414 has one or more mechanical properties that differ from that or those of the center optic 112, 212, 312, and 412, respectively. In some examples of these embodiments, the rim 114, 214, 314 or 414 is made from a different material than the center optic 112, 212, 312, and 412, respectively.

Figure 9A:
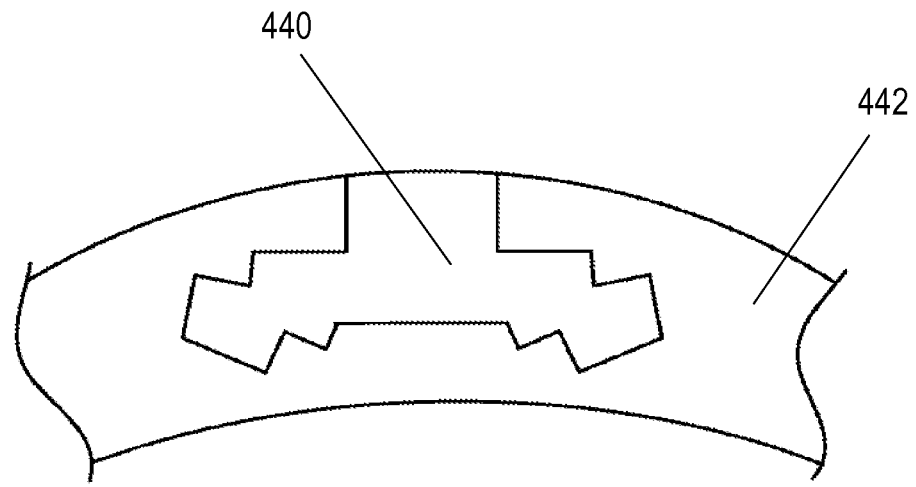
FIG. 9A illustrates that a volume of tissue has been removed from the cornea.
Figure 9B:
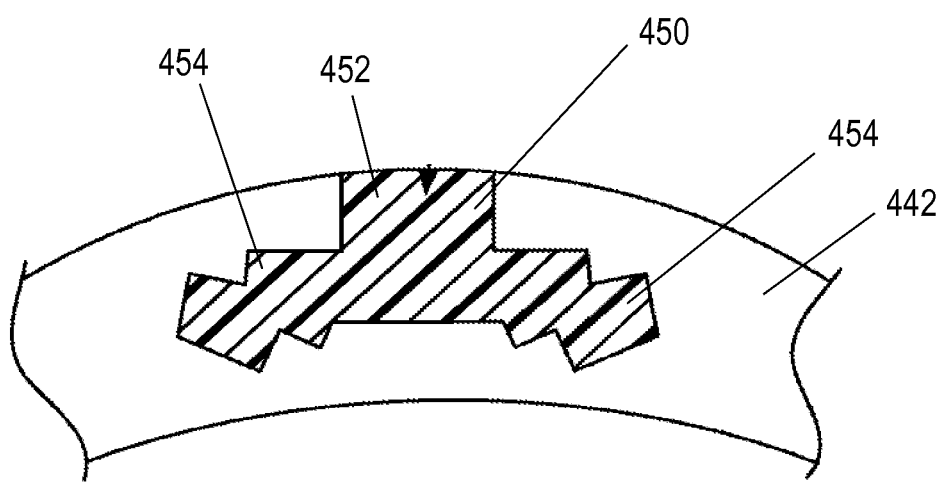
FIG. 9B illustrates a corneal implant that is designed to match the volume of the removed tissue shown in FIG. 9A.

In still further embodiments, FIG. 9A illustrates that a volume of tissue 440 has been removed from the cornea 442. FIG. 9B illustrates a corneal implant 450 that is configured to match the volume of the removed tissue 440 shown in FIG. 9A. In some examples of these embodiments, the rim 454 has one or more mechanical properties that differ from that or those of the center optic 452. In some examples of these embodiments, the rim 454 is made from a different material than the center optic 452.

Figure 6A:
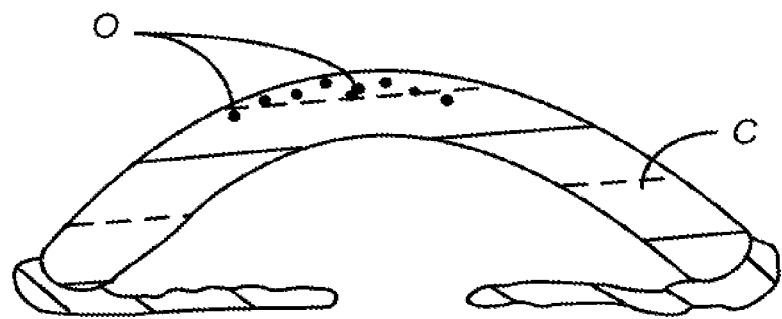
FIGS. 6A through 6F illustrate implantation of the artificial cornea of FIGS. 1-3 into a corneal pocket.
Figure 6B:
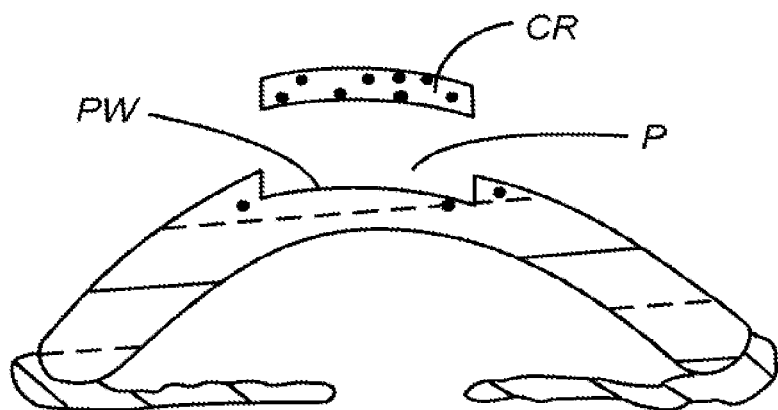
Figure 6C:
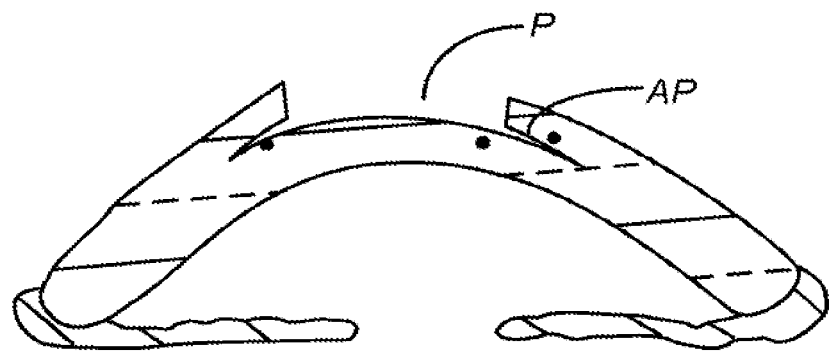
Figure 6D:
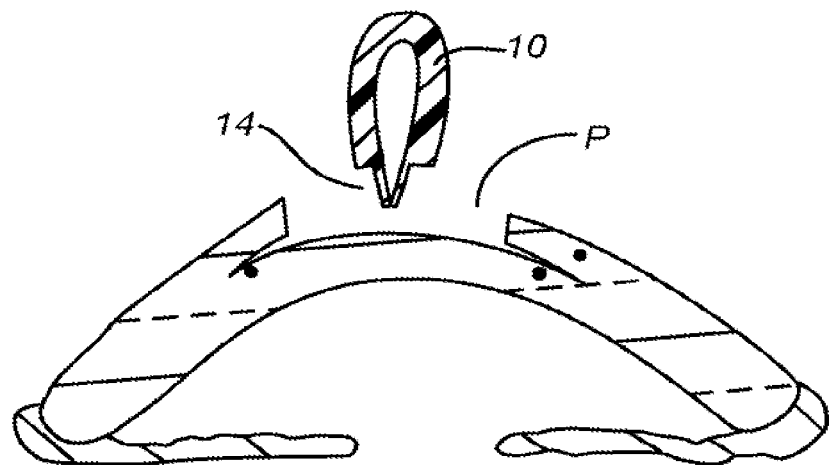

Referring now to FIGS. 6A through 6F, implantation of the artificial cornea 10 of the present disclosure into a cornea C will be described. As illustrated in FIG. 6A, the cornea C having opaque or other optically irregular regions present, typically in its central region, is illustrated. In order to introduce the artificial cornea 10, a central region of the cornea is cut out and removed, as illustrated in FIG. 6B. Cutting may be achieved in a conventional manner, typically using a femtosecond laser, optionally combined with a mechanical trephine, to cut the cylindrical pocket in a posterior direction. In implanting an artificial cornea in accordance with the present disclosure, it is very important that the depth of the pocket be carefully controlled, particularly around the peripheral edge. The depth will typically be controlled at from about 200 μm to 400 μm below the surface of the cornea, leaving a sufficient posterior thickness of the cornea to prevent perforation beneath the pocket for corneas having an average thickness of 500 μm to 600 μm. In cases of abnormally thick corneas, such as commonly found in cases of corneal edema due to endothelial failure, the depth of the pocket may be as much as 800 μm to compensate for the increased thickness of the cornea. The pocket will be formed with a posterior wall PW, as shown in FIG. 6B. After the pocket P has been formed, an annular pocket AP is formed about the peripheral base of the center pocket P, as illustrated in FIG. 6C. Alternatively, a lamellar pocket, wherein the posterior wall PW and the annular pocket AP are continuous, is first created followed by the removal of central region CR to create the anterior opening. The dimensions of the main pocket and annular pocket will be selected to be compatible with the dimensions of the artificial cornea 10 described above. For example, if the artificial cornea has the dimensions set forth in Table 1, then the depth of the pocket should be 200 μm, the diameter of the pocket should be 3.5 mm, and the outer diameter of the annular pocket AP extending around the central pocket P should be 8.5 mm.

Figure 6E:
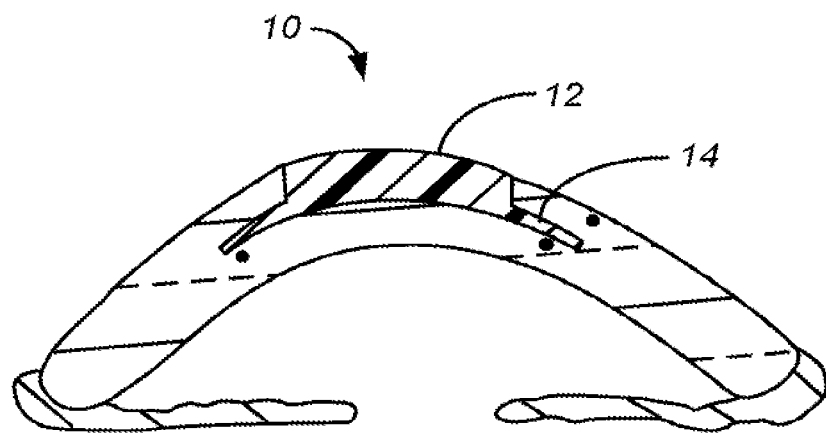

Once the central pocket P and annular pocket AP have been formed, the artificial cornea 10 can be folded or otherwise constrained (i.e. deformed), as illustrated in FIG. 6B, and inserted in a posterior direction into the central pocket P. As the artificial cornea 10 is inserted, the constraint can be released so that the annular rim 14 opens radially outwardly and enters the annular pocket AP, as illustrated in FIG. 6E. The artificial cornea 11 can then optionally be sutured in place, typically using resorbable nylon sutures. Typically, the artificial cornea of the present disclosure will be self-retaining within the cornea even without sutures.

Figure 6F:
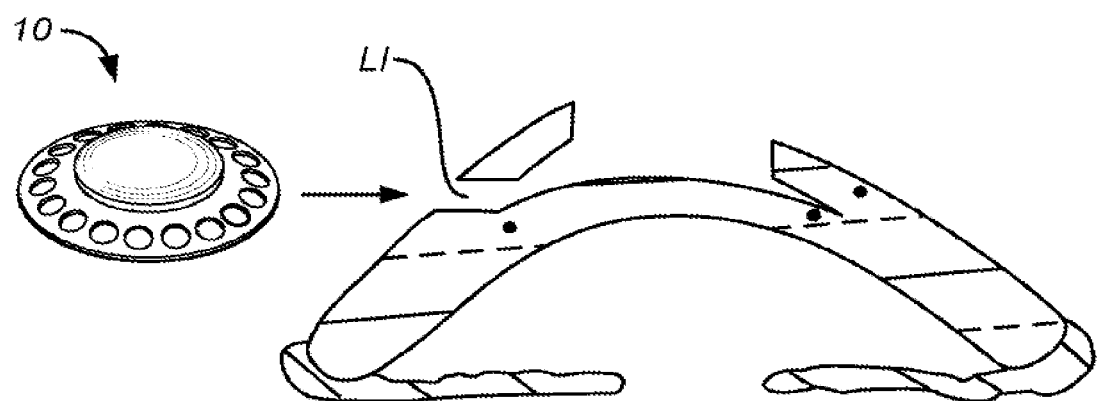

Alternatively, as illustrated in FIG. 6F, the artificial cornea 10 can be introduced through a lateral incision LI formed to provide access. Use of a lateral incision may be selected when, for example, the pocket maker described in commonly owned U.S. Pat. No. 7,223,275, is used for forming the pocket.

Figure 7A:
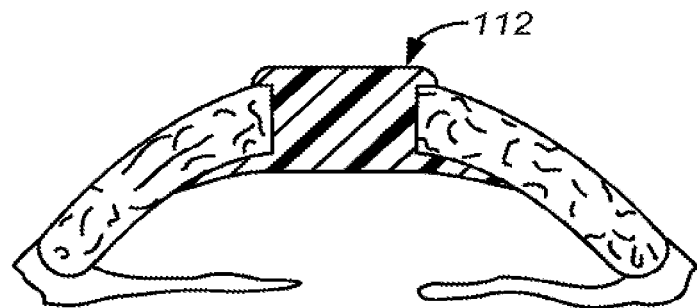
FIGS. 7A through 7C compare the implantation profiles of two prior art artificial corneas with that of the present disclosure.
Figure 7B:
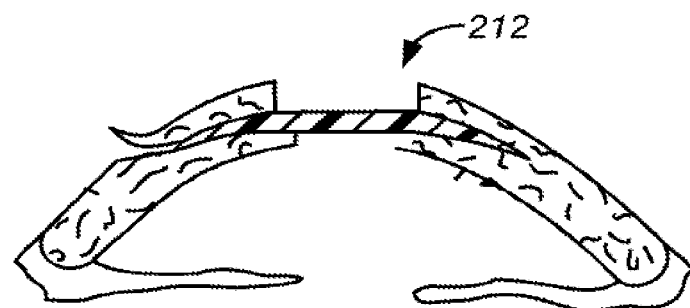
Figure 7C:
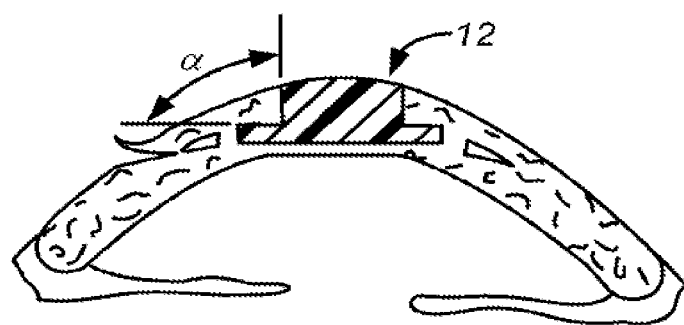

In FIG. 7A the center optic 112 of the Boston Artificial Cornea rises above the surface of the donor carrier cornea which will cause irritation by abrading the inner lining of the patient's eyelid. In FIG. 7B the center optic 212 of the Alphacor™ resides under the surface of the cornea, which produces a divot that will accumulate mucus and debris, thus obscuring the patient's vision. In FIG. 7C the edges of the center optic 12 of the artificial cornea of the present disclosure is at the same level as the surrounding cornea. Additionally there is no gap between the surrounding corneal tissue and the optic because the opening of the cornea is sized to be slightly smaller than the optic diameter, which provides a snug fit. Also note that the angle α of the side of the optic matches the angle of the adjacent incision.

Figure 10:
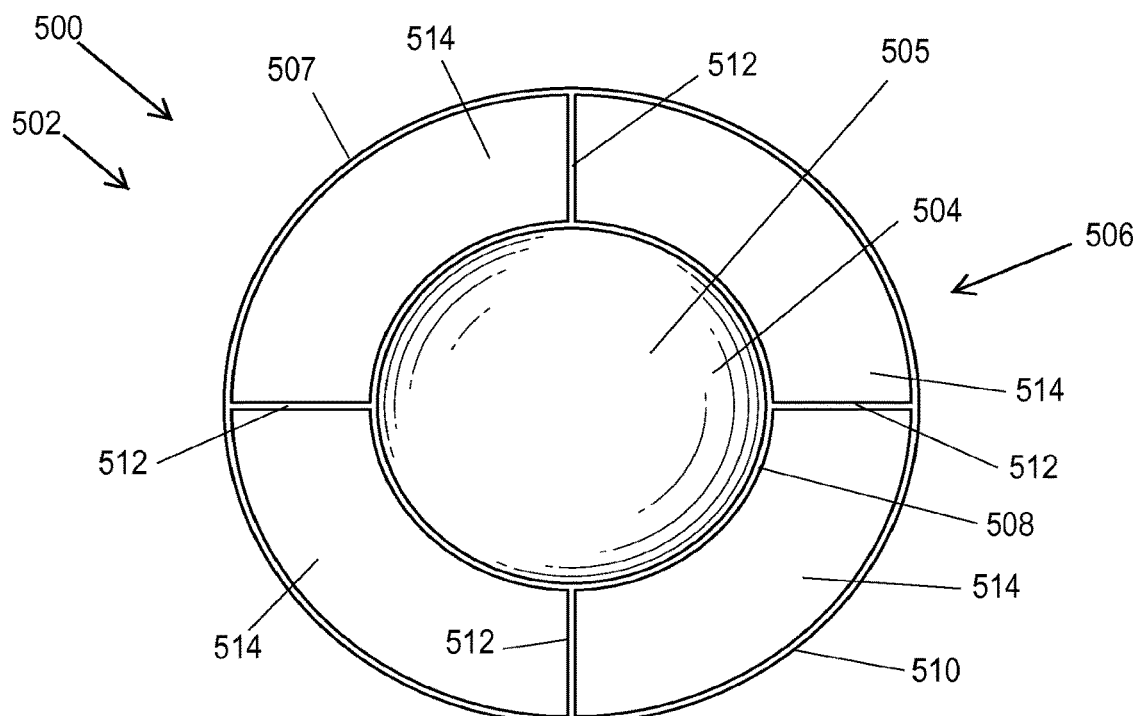
FIG. 10 is a front view (i.e. anterior; facing the exterior of the human body following implantation) of a further embodiment of a corneal implant in accordance with the present disclosure.

FIG. 10 is a front (i.e., anterior) view of a further embodiment of a corneal implant in accordance with the present disclosure shown in a relaxed state. The corneal implant 500 includes an artificial cornea 502, an optical portion 504 having an anterior surface 505, and an anchoring portion 506. In this example the anchoring portion 506 includes a scaffold 507 having an inner ring 508, an outer ring 510 and at least one connecting member 512. Empty space 514 is shown between the inner ring 508 and the outer ring 510.

The artificial cornea 502 is configured to replace excised corneal tissue in a patient's eye. In some examples the artificial cornea 502 is configured to replace a full-thickness portion of corneal tissue; in other examples the artificial cornea 502 is configured to replace a partial-thickness portion of corneal tissue. In some examples, the artificial cornea 502 replaces corneal stromal tissue, which can include an excision from an anterior portion of the stroma, a posterior portion of the cornea, or both an anterior portion and a posterior portion of the cornea. In some examples, the artificial cornea 502 replaces excised corneal tissue anterior to Descemet's membrane, i.e. non-penetrating, partial thickness surgery. In some examples, the artificial cornea 502 replaces a full thickness of excised corneal tissue including Descemet's membrane and endothelium, i.e. penetrating, full thickness surgery. In some examples, the artificial cornea 502 allows for growth of epithelium over an anterior surface (such as anterior surface 505) following implantation. In some of these embodiments, one or more portions of the one or more portions of an anterior surface of the artificial cornea is treated or modified in accordance with disclosures above in order to encourage new epithelial growth over part or the entirety of the anterior surface 505.

In the example corneal implant 500, the optical portion 504 is shaped to restore and/or improve vision in the eye into which it is being implanted. Thus in some examples optical portion 504 is shaped like a lens such that it is capable of refracting light entering the patient's eye. Moreover, the optical portion 504 is transparent or substantially transparent in order to transmit light through the eye. The precise size and shape of the optical portion 504 can vary in accordance with disclosures above. Some examples of suitable materials for the optical portion 504 have been described previously. Generally, the optical portion 504 may be made of any transparent substance and may or may not be reversibly deformable. Thus, in some examples, the optical portion 504 is made from a clear polymer (e.g. silicone, acrylic). In other examples, the optical portion 504 is made from a natural (e.g. from a human or animal source) or synthetic collagen. In still further examples, the optical portion 504 is made from a non-deformable solid such as glass or a crystal, e.g., sapphire or diamond. In yet further examples, the optical portion 504 is made from a plurality of different materials. In some examples, the optical portion has a round perimeter, such as the perimeter of the anterior surface 505 of the optical portion 502. The diameter of such an optical portion 504 is typically in a range from about 3 mm to about 9 mm. In alternative examples, the optical portion 502 has a polygonal or irregular perimeter in which the largest distance between two points on the perimeter of the polygon is in a range from about 3 mm to about 9 mm. Depending on the material(s) selected for the optical portion 502, the optical portion 502 can be manufactured in any suitable fashion, e.g. through machining the optical portion 502 from a block of material, or molding (e.g. injection molding).

The example optical portion 504 includes an anterior surface 505. Depending on the patient and the particular portion of the cornea being excised and replaced, the anterior surface 505 can be embedded in stroma, can abut the anterior surface of the stroma, or can be situated anterior to Bowman's layer. In some examples the anterior surface 505 is configured based on the refractive properties of the other portions of the patient's eye in which it is being implanted in order to provide improved or enhanced vision to the eye. In some examples the anterior surface 505 is convex. The degree of convexity may modified to accommodate the specific optical characteristics of the patient's eye.

The example anchoring portion 506 extends from the optical portion. The primary purpose of the anchoring portion 506 is to retain the corneal implant 500 in place in the eye and to avoid extrusion of the corneal implant 500, ideally without the need for sutures or other securing means (e.g. glue), i.e., the corneal implant 500 should be self-retaining. In some examples, the anchoring portion 506 surrounds the optical portion 504. In some examples, the anchoring portion 506 includes a frame or scaffold structure consisting of mostly empty space, such as empty space 514 shown in FIG. 10. In this example the anchoring portion 506 is a scaffold 507 that includes an inner ring 508 that surrounds, contacts, and is mounted to a wall of the optical portion 504, and an outer ring 510 that is wider than the inner ring. The inner ring 508 and the outer ring 510 are connected by one or more connecting members 512. In some examples, there is just one connecting member 512. In other examples, there are two, three, four, or more connecting members 512. In some examples containing multiple connecting members 512, the connecting members 512 are evenly spaced from one another within the anchoring portion 506. Between adjacent connecting members 512 is empty space 514.

The various aspects of the anchoring portion 506 (such as the inner ring 508, the outer ring 510, and the one or more connecting members 512) can be thicker or thinner depending on the specific characteristics desired for the corneal implant 500, such as strength, size, weight, materials, reversible deformability, self-retention capability of the artificial cornea 502 within a patient's cornea, and so forth. For example, one or more of the various aspects of the anchoring portion 506 can be made thinner to increase or maximize the amount of the empty space 514 and/or to enhance the self-retention capability of the artificial cornea 502 within a patient's cornea. In addition, an anchoring portion 506 made of thinner components can be more flexible than an anchoring portion comprising thicker components. In some examples, the outer ring 510 of the anchoring portion 506 is in a range from about 1 mm to about 4.5 mm away from optical portion 504 when the artificial cornea 502 is in a relaxed state. The empty space 514 allows for improved corneal nutrition, as oxygen and other nutritive molecules can pass easily from the anterior portion of the cornea to the posterior portion of the cornea and vice versa through the empty space 514 in the corneal implant 500. To be clear, the empty space 514 is not empty following implantation into a cornea, but rather becomes filled with the patient's natural, surrounding tissue. This would occur, for example, if the anchoring portion 506 of the artificial cornea 502 is implanted in a corneal pocket surrounding the excised tissue of the cornea (the optical portion 504 would replace the excised tissue).

The anchoring portion 506 can be machined or molded as appropriate from any or from multiple of a variety of reversibly deformable materials such as those described above. In addition, the scaffold 507 can be manufactured as a single, integrated piece or as multiple pieces that are then joined together. Different pieces (such as the inner ring 508, the outer ring 510, and the connecting members 512) of the scaffold 507 can be joined together through any suitable means, such as glue, welding, chemical bonding or mechanical fitting.

Although including the empty space 514 within the anchoring portion 506 of the artificial cornea 502 theoretically reduces structural stability of the anchoring portion 506 and, correspondingly, its ability to retain and anchor the artificial cornea 502 within a patient's eye, the particular structure of anchoring portion 506 (e.g. the scaffold 507), and/or the fact that the anchoring material can be stronger or otherwise more structurally sound than the optical portion 504 overcomes any such perceived disadvantage to utilizing a largely open-space anchoring portion, while providing the advantage of improved nutritive permeability.

In some embodiments the optical portion 504 is made from a material having one or more different mechanical properties from the anchoring portion 506. Examples of such mechanical properties include, but are not limited to: compressive strength (stress a material can withstand before compressive failure); creep (the slow and gradual deformation of an object with respect to time); ductility (the ability of a material to deform under tensile load); elongation-to-break ratio; fatigue limit (maximum stress a material can withstand under repeated loading); flexural modulus; flexural strength; fracture toughness (energy absorbed by unit area before the material fractures); hardness (the ability to withstand surface indentation); plasticity (the ability of a material to undergo irreversible deformations); Poisson's ratio (ratio of lateral strain to axial strain); resilience (the ability of a material to absorb energy when it is deformed elastically); shear strain; shear strength; shear modulus (ratio of shear strength to shear strain); specific modulus (modulus per unit volume); specific strength (strength per unit density); tensile strength (maximum tensile stress a material can withstand before failure); yield strength (the stress at which a material starts to yield); Young's modulus (ratio of linear stress to linear strain); coefficient of friction on the material surface; and coefficient of restitution.

Choosing materials with different mechanical properties for the optical portion 504 and the anchoring portion 506 results in artificial corneas 502 having a variety of different characteristics. For example, an artificial cornea 502 having a relatively stiff (e.g., higher Young's modulus) optical portion 504 improves the optical regularity of the refracting surface (e.g. the anterior surface 505) of the optical portion 504, resulting in better vision for the patient. On the other hand, an artificial cornea 502 having a relatively flexible (e.g., lower Young's modulus) optical portion 504 may result in less than optimal optical regularity of the refracting surface while at the same time providing the patient with a more comfortable implant that may require less adaption following implantation. Conversely, a stiffer optical portion 504 optic may require the use of a soft bandage contact lens over the optical portion 504 in order to provide an acceptable comfort level for the patient.

With respect to the mechanical properties of the anchoring portion 506, having a relatively stiff (e.g., higher Young's modulus) anchoring portion 506 allows for an anchoring portion 506 made of mostly empty space (e.g. empty space 514), which is advantageous for reasons such as those discussed above, while still being capable of providing secure and/or self-retaining anchoring of the artificial cornea 502 within a corneal pocket. On the other hand, having a relatively flexible anchoring portion may improve patient comfort but could reduce secure retention.

It is advantageous to provide a reversibly deformable artificial cornea 502 having a plurality of regions with different mechanical properties in order optimize different characteristics of the artificial cornea, such as optical quality, comfort, and retention. In some specific example embodiments it is advantageous to provide an artificial cornea 502 having an optical portion 504 with mechanical properties that differ from those of its anchoring portion 506 in order to optimize different characteristics of the implant, such as optical quality, comfort and retention.

Providing an artificial cornea 502 with an optical portion 504 having a first set of mechanical properties, and an anchoring portion 506 having a second set of mechanical properties, can be accomplished by, for example, differentiated material selection and/or differentiated treatment of the same material as described above. In some embodiments of the artificial cornea 502 in a relaxed state the optical portion 504 is made of crystal sapphire and has a diameter in a range from about 3 mm to about 5 mm, a thickness (from anterior surface 505 to a posterior end 522 (see FIG. 11)) in a range from about 300 μm to about 500 μm, a refractive index in a range from about 1.7 to about 1.8, a Young's modulus at about 25° C. in a range from about 300 GPa to about 600 GPa parallel to the corneal axis $A_1$ (FIG. 14), a modulus of rigidity (shear modulus) in a range from about 100 GPa to about 300 GPa; a Poisson's ratio in a range from about 0.2 to about 0.4 depending on orientation, a flexural strength parallel to the corneal axis $A_1$ (FIG. 14) at about 25° C. in a range from about 900 MPa to about 1200 MPa, a flexural strength perpendicular to the corneal axis $A_1$ (FIG. 14) at about 25° C. in a range from about 500 MPa to about 1000 MPa, a compressive strength at about 25° C. in a range from about 1.5 GPa to about 2.5 GPa, a hardness (at about 20° C. to about 25° C.) in a range from about 8 to about 10 (on the Mohs scale) corresponding to a range from about 1800 Knoop to about 2000 Knoop parallel to the corneal axis $A_1$ (FIG. 14) and a range from about 2100 Knoop to about 2300 Knoop perpendicular to the corneal axis $A_1$ (FIG. 14).

In some embodiments of the artificial cornea 502 in a relaxed state, the anchoring portion 506 is made of a nickel-titanium alloy with maximum diameter in a range from about 5 mm to about 10 mm, an ultimate tensile strength in a range from about 600 MPa to about 1200 MPa, an elongation to fracture in a range from about 10 percent to about 20 percent, a yield strength (at about 5° C.) in a range from about 50 MPa to about 150 MPa, an elastic modulus at about 5° C. in a range from about 20 GPa to about 40 GPa, and a Poisson's ratio in a range from about 0.2 to about 0.4.

In a particular example of the artificial cornea 502 in the relaxed state, the optical portion 504 has a diameter of about 4 mm, a thickness (from anterior surface 505 to a posterior end 522 (see FIG. 11)) of about 400 μm, a refractive index of about 1.7682, a Young's modulus at about 25° C. of about 435 GPa parallel to the corneal axis $A_1$ (FIG. 14), a modulus of rigidity (shear modulus) of about 175 GPa, a Poisson's ratio in a range from about 0.27 to about 0.30 depending on orientation, a flexural strength at about 25° C. of about 1035 MPa parallel to the corneal axis $A_1$ (FIG. 14) and of about 760 MPa perpendicular to the corneal axis $A_1$ (FIG. 14), a compressive strength at about 25° C. of about 2 GPa, a hardness at about 20° C.-25° C. of about 9 (Mohs scale) corresponding to about 1900 Knoop parallel to the corneal axis $A_1$ (FIG. 14) and about 2200 Knoop perpendicular to the corneal axis $A_1$ (FIG. 14); and an anchoring portion 506 made of nickel-titanium alloy with a maximum diameter of about 7 mm, an ultimate tensile strength in a range from about 754 MPa to about 960 MPa, an elongation to fracture of about 15.5 percent, a yield strength at about 5° C. of about 100 MPa, an elastic modulus at about 5° C. of about 28 GPa, and a Poisson's ratio of about 0.3.

The foregoing particular example would allow the implantation of an artificial cornea 502 having an essentially perfect optical surface (corresponding to the anterior surface 505 of the optical portion 504) into the cornea (sapphire is frequently used in the most precise optical applications such as for focusing lasers). In addition, the nickel titanium alloy anchoring portion 506 is sufficiently flexible that the anchoring portion of the artificial cornea can be reversibly deformable and allow its implantation through a corneal incision that is as small as (or smaller than) half of the diameter of the entire artificial cornea in its relaxed state. Another particularly useful property of a nickel-titanium alloy is that it can be manufactured to have shape-memory so that the anchoring portion 506 can be highly malleable at a cool temperature (e.g., approximately 5° C.) and will then return to its relaxed state after deformation. In practice, a surgeon can soak the artificial cornea 502 in chilled sterile water (e.g., approximately 5° C.) and easily insert the anchoring portion 506 into the corneal recesses and then watch as the anchoring portion 506 automatically expands into its relaxed state to secure the artificial cornea 502 in the cornea as it approaches body temperature (approximately 37° C.).

Figure 11:
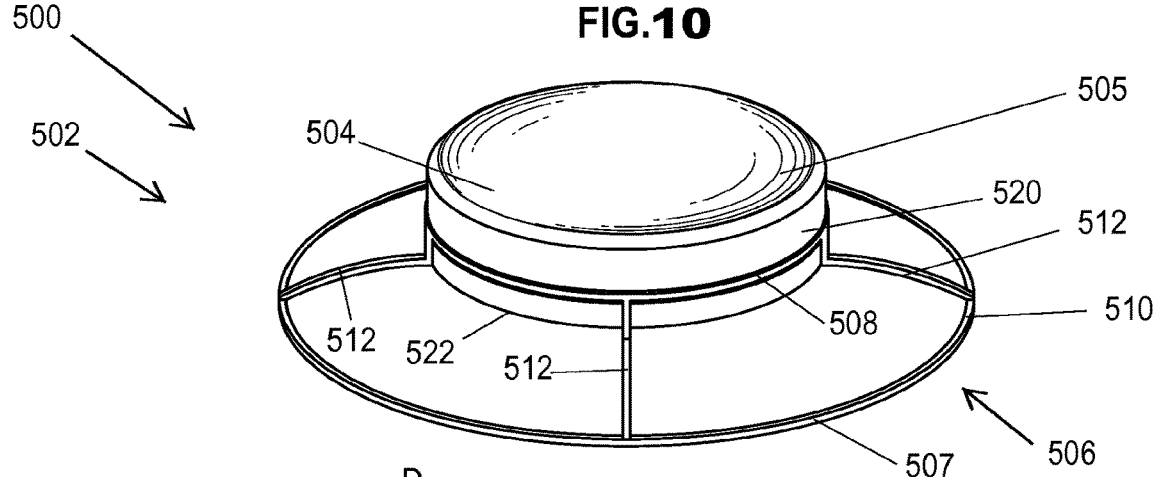
FIG. 11 is a front perspective view of the corneal implant of FIG. 10.

FIG. 11 is a front perspective view of the corneal implant 500 of FIG. 10 shown in a relaxed state. The example corneal implant 500 includes an artificial cornea 502, an optical portion 504 having an anterior surface 505, an anchoring portion 506 having a scaffold 507, an inner ring 508, an outer ring 510, at least one connecting member 512, and empty space 514 between the inner ring 508 and the outer ring 510, as discussed above. In addition, in this example the optical portion 504 includes an exterior side wall 520 and a posterior end 522.

The exterior side wall 520 extends around the entirety of the optical portion 504. In this example, the inner ring 508 of the anchoring portion 506 mates with the exterior side wall 520 between the anterior surface 505 and the posterior end 522 of the optical portion 504 in order to join the optical portion 504 to the anchoring portion 506. Also in this example, the outer ring 510 is behind (posterior to) the inner ring 508 and approximately even with the posterior end 522 of the anchoring portion 506. In alternative embodiments, when the artificial cornea 502 is in a relaxed state, the outer ring 510 and the inner ring 508 lie within or approximately within the same plane. In some examples, such a plane intersects the optical portion 504 at a location between the anterior surface 505 and the posterior end 522. Thus, it should be appreciated that the connecting members 512 may be any suitable shape and configuration to connect the inner ring 508 to the outer ring 510. In the example shown in FIG. 11, each of the connecting members is approximately L-shaped. In an alternative non-limiting example, one or more of the connecting members 512 is linear. In some examples, one or more portions of one or more connecting members 512 is straight or curved.

In some examples, the optical portion 504 and the anchoring portion 506 are manufactured separately and joined together for assembly. In other examples, the optical portion 504 and the anchoring portion 506 are manufactured together as a single piece and then one or more regions of the artificial cornea 502 are exposed to one or more material treatments.

Figure 12:
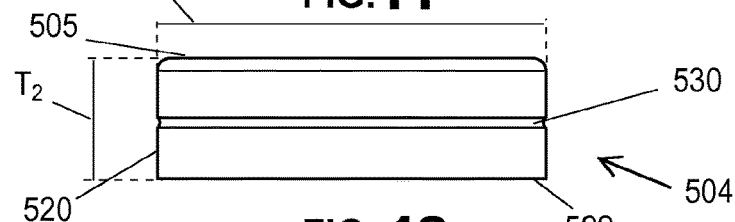
FIG. 12 is a side view of an example optical portion of the corneal implant of FIG. 10.

FIG. 12 is a side view of an example optical portion 504 of the corneal implant of FIG. 10 shown in a relaxed state. The example optical portion 504 includes the anterior surface 505, the exterior side wall 520, and the posterior end 522 as discussed above. In addition, in this example the optical portion 504 includes a groove 530.

The groove 530 is disposed in the exterior side wall 520 between the anterior surface 505 and the posterior end 522 of the optical portion 504. In this example, the groove is continuous and extends around the entirety of the exterior side wall 520. In alternative examples, the groove 530 is segmented or otherwise discontinuous. The inner ring 508 is mated with or otherwise coupled to the groove 530. In some examples this is accomplished by a mechanical or frictional fit, the groove 530 being suitably sized to receive the inner ring 508 in a mating fashion. In addition, glue or other attachment means can be used in addition to, or in place of, the groove 530, to secure the inner ring 508 to the optical portion 504. The precise location of the groove 530 in the exterior side wall 520 of the optical portion 504 may be selected based on the specific conditions and parameters presented by the specific patient, excision, and implantation in question.

Figure 13:
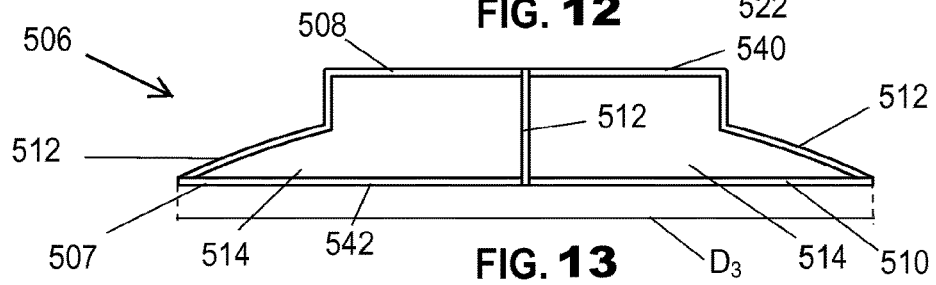
FIG. 13 is a side view of an example anchoring portion of the corneal implant of FIG. 10.

FIG. 13 is a side view of an example anchoring portion 506 of the corneal implant of FIG. 10 shown in a relaxed state. The example anchoring portion 506 includes a scaffold 507 having an inner ring 508, an outer ring 510, one or more connecting members 512, and empty space 514 as discussed above. In addition, in this example, the anchoring portion 506 includes an anterior end 540 and a posterior end 542. In some examples, the posterior end 542 is behind (i.e., posterior to) the posterior end 522 (FIG. 11) of the optical portion 504 (FIG. 11) when the artificial cornea 502 (FIG. 11) is in a relaxed state. In some examples, the posterior end 542 is flush with the posterior end 522 when the artificial cornea 502 is in a relaxed state. In yet further examples, the inner ring 508 and the outer ring 510 are in the same plane when the artificial cornea 502 is in a relaxed state, such that the anterior end 540 and the posterior end 542 of the scaffold 507 are also in the same plane (i.e., the anchoring portion 506 is substantially flat). In any of the foregoing examples, the relative positioning of the anterior end 540 to the posterior end 542 can change when the artificial cornea 502 moves to a deformed stated. This is discussed further in connection with FIGS. 14-15. In alternative examples to the scaffold 507 shown in the figures, the scaffold 507 can include additional retaining rings and/or support structures.

FIG. 14 is a side view of the corneal implant 500 of FIG. 10 showing the implant in an example deformed state in which the anchoring portion is deformed and the optical portion is relaxed; FIG. 15 is a side view of the corneal implant 500 of FIG. 10 showing the implant in a deformed state in which both the anchoring portion and the optical portion are deformed. As shown in FIGS. 14-15, the corneal implant 500 includes an artificial cornea 502; an optical portion 504 having an anterior surface 505, an exterior side wall 520, and a posterior end 522; and an anchoring portion 506 having an inner ring 508, an outer ring 510, one or more connecting members 512, empty space 514, an anterior end 540, and a posterior end 542, as described above.

As shown in FIG. 14, the outer ring 510 and the connecting members 512 have been reversibly deformed, reducing a width of the artificial cornea 502. In this example, the optical portion 504 may or may not be deformable and/or reversibly deformable. The deformation of the outer ring 510 and the connecting members 512 is advantageous prior to implantation of the artificial cornea in to the eye, as the reduced width enables the artificial cornea to be implanted through an incision that is smaller than a width of the artificial cornea in its relaxed state. In some examples, deformation of the artificial cornea 552 allows implantation of the artificial cornea 502 through an incision that is less than half a width of the artificial cornea in its relaxed state. A smaller incision decreases the chances of extrusion post-implantation and increases the chances of self-retention (i.e. without sutures, glue, or other attachment means). Once inserted through the incision, the artificial cornea 502 returns partially or entirely to its relaxed state with the optical portion filling (partially or completely) an excision in the corneal tissue, and at least a portion of the outer ring 510 and the connecting members 512 disposed within a corneal pocket skirting the excision.

As shown in FIG. 15, the outer ring 510, the connecting members 512, and the optical portion 504 have all been reversibly deformed, further reducing a width of the artificial cornea 502 (as compared with FIG. 14). Thus, in the example shown in FIG. 15, both the optical portion 504 and the anchoring portion 506 are reversibly deformable. As with the deformation of FIG. 14, this deformation is advantageous prior to implantation of the artificial cornea into the eye, as the reduced width enables the artificial cornea to be implanted through an incision that is smaller than a width of the artificial cornea in its relaxed state. A smaller incision (in this case, even smaller than the incision required to implant the deformed artificial cornea in FIG. 14) decreases the chances of extrusion post-implantation and increases the chances of self-retention (i.e. without sutures, glue, or other means). Once inserted through the incision, the artificial cornea 502 returns partially or entirely to its relaxed state with the optical portion 504 filling (partially or completely) an excision in the corneal tissue, and at least a portion of the outer ring 510 and the connecting members 512 disposed within a corneal pocket around the excision.

FIG. 16 is a side cross-sectional view of a further embodiment of a corneal implant in accordance with the present disclosure showing the corneal implant in a relaxed state; FIG. 17 is a front (i.e. anterior) view of the corneal implant of FIG. 16 showing the corneal implant in a relaxed state. As shown in FIGS. 16-17, the corneal implant 550 includes an artificial cornea 552, an optical portion 554 having an anterior surface 556, a posterior end 558, and an exterior side wall 560. The corneal implant 550 also includes an anchoring portion 562, which includes a skirt 564.

In some examples the artificial cornea 552 is configured to replace a full-thickness portion of corneal tissue; in other examples the artificial cornea 552 is configured to replace a partial-thickness portion of corneal tissue. In some examples, the artificial cornea 552 replaces corneal stromal tissue, which can include an excision from an anterior portion of the stroma, a posterior portion of the cornea, or both an anterior portion and a posterior portion of the cornea. In some examples, the artificial cornea 552 replaces excised corneal tissue anterior to Descemet's membrane, i.e. non-penetrating, partial thickness surgery. In some examples, the artificial cornea 552 replaces a full thickness of excised corneal tissue including Descemet's membrane and endothelium, i.e. penetrating, full thickness surgery. In some examples, the artificial cornea 552 allows for growth of epithelium over an anterior surface following implantation. In some of these embodiments, one or more portions of the one or more portions of an anterior surface of the artificial cornea 552 is treated or modified in accordance with disclosures above in order to encourage new epithelial growth.

In this example artificial cornea 552, the skirt 564 surrounds the optical portion 554, extending from the exterior side wall 560 of the optical portion 554 at a location between the anterior surface 556 and the posterior end 558 of the optical portion 554. In some examples, one of either the optical portion 554 and the anchoring portion 562 is reversibly deformable to allow implantation of the artificial cornea 552 through an incision that is less than a width of the artificial cornea 552 in its relaxed state. In some examples, deformation of the artificial cornea 552 allows implantation of the artificial cornea 552 through an incision that is less than half a width of the artificial cornea in its relaxed state. In other examples, both the optical portion 554 and the anchoring portion 562 are reversibly deformable. Once inserted through the incision in the eye, the artificial cornea 552 returns partially or entirely to its relaxed state with the optical portion filling (partially or completely) an excision in the corneal tissue, and at least a portion of the skirt 564 disposed within a corneal pocket that partially or completely surrounds the excision.

The skirt 564 may be made thicker or thinner (as measured from anterior to posterior) and wider or narrower (as measured from the optical portion 554 outward from the optical portion 554) depending on the parameters and characteristics of the patient and the particular surgery to be performed. The skirt 564 is implanted in a corneal pocket surrounding a corneal excision, while the optical portion 554, after implantation, fills (partially or entirely) the excised portion of the cornea. In this example embodiment, the skirt 564 and the optical portion 554 are constructed of materials with one or more disparate mechanical properties, including but not limited to the mechanical properties described above. In some examples, this is accomplished by manufacturing the skirt 564 and the optical portion 554 from different materials. Additionally, or alternatively, the skirt 564 and optical portion 554 are applied with different material treatments from each other, such as mechanical, heat, radiation (e.g., electromagnetic radiation), and/or chemical treatments. In some of these examples, only one of the optical portion 554 and anchoring portion 562, or a portion thereof is treated in this manner to achieve a reversibly deformable artificial cornea 552 having regions with different mechanical properties.

The artificial cornea 552 is machined or molded as a single, monolithic, unit. Alternatively, the skirt 564 and the optical portion 554 are manufactured separately and then joined together through any suitable means, such as glue, welding, and/or a mechanical/frictional fit.

Figure 18:
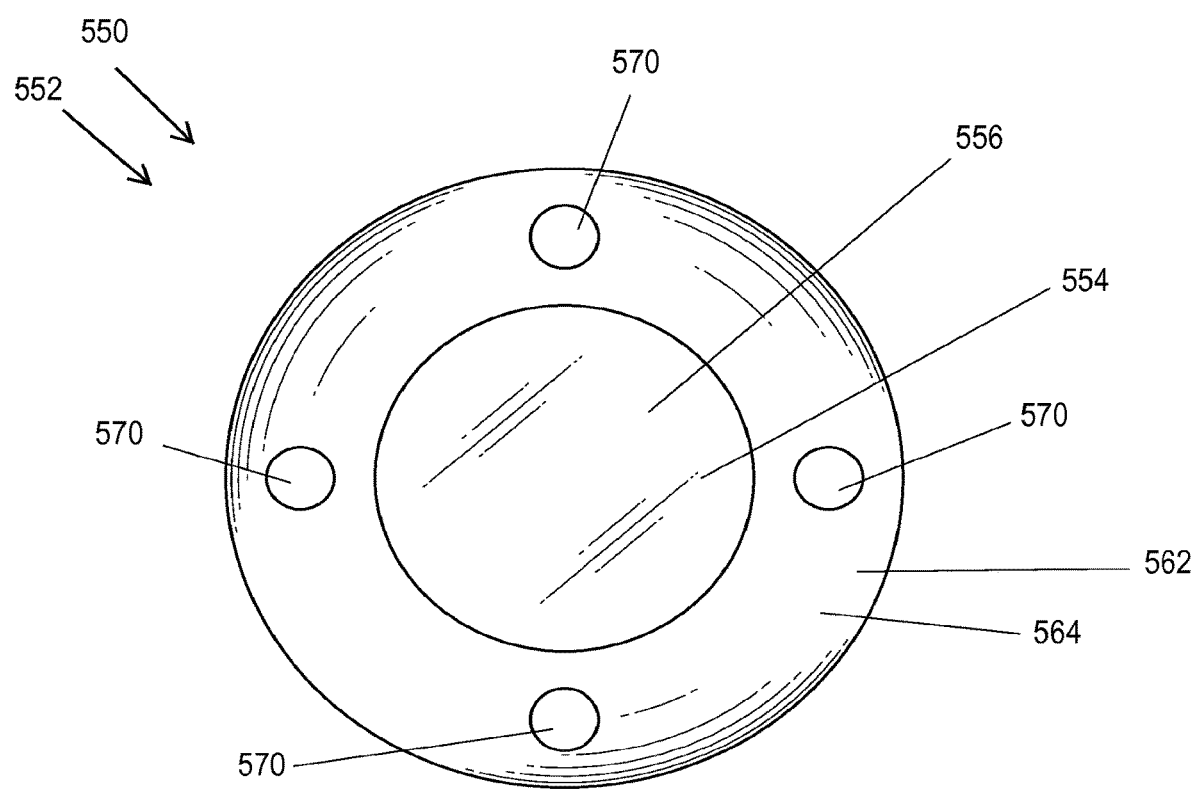
FIG. 18 is a front (i.e. anterior) view of a modified version of the corneal implant embodiment shown in FIGS. 16-17.

FIG. 18 is a front (i.e. anterior) view of a modified version of the corneal implant embodiment shown in FIGS. 16-17. The corneal implant 550 includes an artificial cornea 552, an optical portion 554 having an anterior surface 556; and an anchoring portion 562 including a skirt 564, as discussed above. In addition, in this embodiment the skirt includes one or more apertures 570. The one or more apertures 570 allow for the passage of oxygen and nutrients in accordance with the disclosure above. The skirt 564 (or a portion thereof) and the optical portion 554 (or a portion thereof) have one or more different mechanical properties, as described above in connection with FIGS. 16-17.

While the above is a complete description of certain embodiments of the invention, various alternatives, modifications, and equivalents may be used. Therefore, the above description should not be taken as limiting the scope of the invention which is defined by the appended claims.

The invention claimed is:

1. A reversibly deformable artificial cornea comprising:
   a monolithic body having a diameter between 4 mm and 10 mm and comprising a center optic surrounded by an annular rim, wherein the center optic has a cylindrical outer peripheral wall having a diameter in the range from 3 mm to 9 mm and an optic height in the range from 200 µm to 800 µm, and the rim has a width in the range from 0.5 mm to 4.5 mm and a median thickness in the range from 50 µm to 200 µm;
   wherein the monolithic body is comprised of a polymeric hydrogel having a Young's modulus in the range from 0.3 MPa to 100 MPa when fully hydrated;
   wherein the center optic is capable of refracting light entering the patient's eye;
   wherein the annular rim circumscribes an edge of the center optic;
   wherein the artificial cornea comprises a relaxed state and a deformed state, and being reversibly deformable such that the artificial cornea can return to the relaxed state from the deformed state without said artificial cornea breaking;
   wherein the diameter of the center optic is selected to be larger than a diameter of a central anterior opening of a space in a cornea in which the artificial cornea is implanted, the space being formed from an excised portion of the cornea; and
   wherein the optic height of the center optic is selected to match a depth of the space to within a tolerance of ±50 µm when the artificial cornea is implanted in the cornea.

2. An artificial cornea as in claim 1, having a tensile strength of at least 1.5 MPa.

3. An artificial cornea as in claim 1, having an elongation to break of at least 100%.

4. An artificial cornea as in claim 1, wherein an angle between the center optic and the rim varies by less than ±10°.

5. An artificial cornea as in claim 1, wherein the rim circumscribes a posterior edge of the center optic.

6. An artificial cornea as in claim 1, wherein at least an anterior surface of the center optic is convexly shaped to provide a refractive power generally equal to a native cornea.

7. An artificial cornea as in claim 6, wherein the center optic provides a refractive power in the range from 30 diopter to 70 diopter when implanted in a cornea.

8. An artificial cornea as in claim 7, wherein both the anterior and posterior surfaces of the center optic are convexly shaped.

9. An artificial cornea as in claim 8, wherein the anterior surface is flatter than the posterior surface.

10. An artificial cornea as in claim 1, wherein the rim has apertures to allow passage of nutrients and oxygen.

11. An artificial cornea as in claim 10, wherein the apertures occupy from 10% to 90% of the annular area of the rim.

12. An artificial cornea as in claim 11, wherein the apertures are round holes disposed uniformly about the annular rim.

13. An artificial cornea as in claim 1, wherein the polymeric hydrogel comprises material selected from the group consisting of hydrophilic acrylic material, a hydrophobic acrylic material, a silicone polymer hydrogel, a collagen polymer hydrogel, and an interpenetrating network hydrogel.

14. An artificial cornea as in claim 1, wherein the polymer hydrogel has an oxygen permeability of at least 3 Barrer.

15. An artificial cornea as in claim 1, wherein the polymer hydrogel comprises a material selected from the group consisting of Lotrafilcon A, Lotrafilcon B, Balafilcon A, Comfilcon A, Senofilcon A, Enfilcon A and Galyfilcon A.

16. An artificial cornea as in claim 1, wherein an annular peripheral region of an anterior face of the center optic promotes epithelial growth while the anterior face within the annular peripheral region inhibits epithelial growth.

17. An artificial cornea as in claim 16, wherein the annular peripheral region is covered with an epithelial growth-promoting material, is roughed, or is porous.

18. An artificial cornea as in claim 16, wherein the anterior face of the center optic within the annular peripheral region is covered with a material that inhibits epithelial growth.

* * * * *